(12) United States Patent
Kawde et al.

(10) Patent No.: US 8,968,825 B1
(45) Date of Patent: Mar. 3, 2015

(54) DISPOSABLE PALLADIUM NANOPARTICLE-MODIFIED GRAPHITE PENCIL ELECTRODE

(71) Applicants: King Fahd University of Petroleum and Minerals, Dhahran (SA); King Abdulaziz City for Science and Technology, Riyadh (SA)

(72) Inventors: Abdel-Nasser Metwally Aly Kawde, Dhahan (SA); MD Abdul Aziz, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 40 days.

(21) Appl. No.: 13/973,974

(22) Filed: Aug. 22, 2013

(51) Int. Cl.
 *B05D 5/12* (2006.01)
 *G01N 27/30* (2006.01)
 *C23C 30/00* (2006.01)

(52) U.S. Cl.
 CPC ............ *G01N 27/308* (2013.01); *C23C 30/00* (2013.01)
 USPC ......... 427/113; 427/125; 427/180; 427/383.1

(58) Field of Classification Search
 USPC ................................. 427/113, 125, 180, 383.1
 See application file for complete search history.

(56) References Cited

U.S. PATENT DOCUMENTS

| 5,540,828 A | 7/1996 | Yacynych |
| 7,538,062 B1 * | 5/2009 | Dai et al. ...................... 502/185 |
| 8,349,547 B1 * | 1/2013 | Burckel et al. ................ 430/322 |
| 2007/0144902 A1 | 6/2007 | Schuelein et al. |
| 2009/0084159 A1 * | 4/2009 | Sun et al. ...................... 73/31.05 |
| 2011/0031134 A1 * | 2/2011 | Tacchini et al. ............ 205/785.5 |
| 2011/0139636 A1 | 6/2011 | Lai et al. |

OTHER PUBLICATIONS

Lu, Li-Min et al., "In Situ Synthesis of Palladium Nanoparticle-Graphene Nanohybrids and Their Application in Nonenzymatic Glucose Biosensors", Biosensors and Bioelectronics, 26, 3500-3504, 2011.
Wang, Joseph et al., "Pencil-Based Renewable Biosensor for Label-Free Electrochemical Detection of DNA Hybridization", Analytica Chimica Acta 431, 219-224, 2001.

* cited by examiner

*Primary Examiner* — Brian K Talbot
(74) *Attorney, Agent, or Firm* — Richard C Litman (57) ABSTRACT

The disposable palladium nanoparticle-modified graphite pencil electrode (PdNP-GPE) is a graphite pencil electrode having palladium nanoparticles disposed on the surface of the electrode. The electrode is prepared by adding ascorbic acid to an aqueous solution of ammonium tetrachloropalladate(II) $[(NH_4)_2PdCl_4]$ at room temperature to form the palladium nanoparticles (PdNPs), immersing a GPE in the aqueous solution of PdNPs, and heating the solution to about 75° C. to deposit the PdNPs on the GPE. The palladium nanoparticle modified graphite pencil electrode may be used in an electrochemical cell for quantitative analysis of hydrogen peroxide content in an unknown solution.

3 Claims, 9 Drawing Sheets

DISPOSABLE PALLADIUM NANOPARTICLE-MODIFIED GRAPHITE PENCIL ELECTRODE

FIELD OF THE INVENTION

The present invention relates to electrodes, and particularly to a disposable palladium nanoparticle-modified graphite pencil electrode, an electrochemical cell including the disposable palladium nanoparticle-modified graphite pencil electrode, and a method of making and using a disposable palladium nanoparticle-modified graphite pencil electrode.

BACKGROUND OF THE INVENTION

Hydrogen peroxide ($H_2O_2$) is an important analyte in many fields, such as food, pharmaceuticals, chemical, clinical, printing, and environments, while also being a byproduct in various enzymatic reactions of many peroxidase enzymes, such as glucose oxidase and lactate oxidase. $H_2O_2$ is extremely toxic to living organisms. Therefore, development of simple, sensitive, inexpensive, disposable and accurate sensors for $H_2O_2$ detection is very important.

Electrochemical methods of sensing $H_2O_2$ have attracted much attention due to their simplicity, sensitivity and portability. However, conventional electrodes showed poor electrocatalytic properties towards the electrochemical reaction of $H_2O_2$. As a result, many sensitive hydrogen peroxide enzyme-based sensors (e.g. HRP-, myoglobin-, cytochrome C-modified electrodes) were developed with high catalytic properties. Nevertheless, due to complicated enzyme immobilization procedures, instability, and the high cost of the enzyme and/or expensive substrates, the use of enzyme-modified electrodes for the detection of $H_2O_2$ has its limitations.

Nanomaterials that have high electrocatalytic properties, a high surface-to-volume ratio, high stability, and low cost are being used on various electrode surface modifications. For instance, palladium nanoparticles (PdNPs) embedded into a hierarchically porous $TiO_2$ hollow spheres-modified glassy carbon electrode (GCE), a multi-walled carbon nanotube-PdNPs-modified GCE, a multi-walled carbon nanotube-Pt-NPs-modified GCE, a carbon nanotube-wired CuO nanoflower-modified GCE, a composite of carbon nanotube and silver NP-modified carbon ceramic electrode, a gold NP-modified indium-tin oxide electrode, and silver NP-modified carbon ion liquid electrode have been applied for the electrochemical detection of $H_2O_2$.

Platinum, gold, and glassy carbon conventional electrodes are expensive and show high background currents, unlike the graphite pencil electrode (GPE), which has a renewable surface and low cost, and which gives a relatively low background current. However, due to the poor electrocatalytic properties of the GPE towards the electrochemical reaction of many electroactive molecules, the modification of GPE with a particular electrocatalyst is required for fabricating a sensitive sensor. A PdNP-modified electrode exhibits good electrocatalytic properties for a large number of electroactive molecules, such as catecholamine neurotransmitters, methanol, formic acid and hydrogen peroxide.

Thus, a disposable palladium nanoparticle-modified graphite pencil electrode solving the aforementioned problems is desired.

SUMMARY OF THE INVENTION

The disposable palladium nanoparticle-modified graphite pencil electrode (PdNP-modified GPE) is a graphite pencil electrode having palladium nanoparticles disposed on the surface of the electrode. The electrode is prepared by adding ascorbic acid to an aqueous solution of ammonium tetrachloropalladate(II) [$(NH_4)_2PdCl_4$] at room temperature to form the palladium nanoparticles (PdNPs), immersing a GPE in the aqueous solution of PdNPs, and heating the solution to about 75° C. to deposit the PdNPs on the GPE. The palladium nanoparticle modified graphite pencil electrode may be used in an electrochemical cell for quantitative analysis of hydrogen peroxide content in an unknown solution.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The disposable palladium nanoparticle-modified graphite pencil electrode is a graphite pencil electrode having nanoparticles of palladium deposited on the surface of the electrode.

The electrode may be used in an electrochemical cell having a palladium nanoparticle modified graphite pencil electrode as a working electrode; a platinum wire as a counter electrode; and Ag/AgCl (Sat KCl) as a reference electrode.

The disposable palladium nanoparticle-modified graphite pencil electrode can be made by a method comprising the following steps: mixing aqueous solutions of ascorbic acid (AA) and ammonium tetrachloropalladate(II) to form a palladium nanoparticle (PdNP) solution; immersing a bare graphite pencil lead (graphite pencil electrode or GPE) in a test tube containing the synthesized PdNP solution; and placing the test tube in a preheated water bath at about 75° C. to form the disposable palladium nanoparticle-modified graphite pencil electrode (PdNP-GPE).

Figure 1:
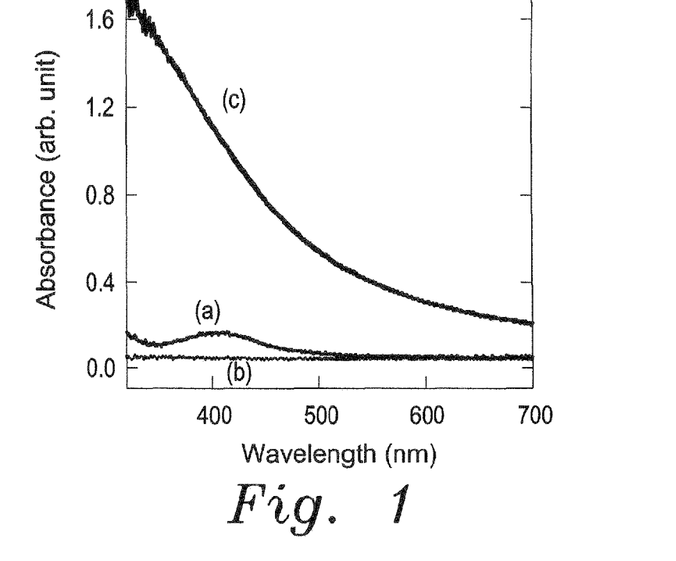
FIG. 1 shows the UV-visible spectra of aqueous solutions of (a) 0.5 mM $(NH_4)_2PdCl_4$; (b) 0.55 mM ascorbic and (c) PdNPs.

The aqueous solution of PdNPs was prepared simply by adding AA (ascorbic acid) (aq.) to $(NH_4)_2PdCl_4$ (aq.) while being stirred at RT (room temperature). Upon addition of AA (aq.) to $(NH_4)_2PdCl_4$ (aq.), the color of the solution started to change from pale yellow to light dark brown, and finally became dark brown after 15 min of stirring. This color change is one of the characteristics of PdNPs formation. A UV-Vis spectrum was recorded using the prepared PdNPs solution (FIG. 1 part c). The UV experiments were performed using a Cintra 303 spectrophotometer. For comparison, the UV-Vis spectra of 0.5 mM $(NH_4)_2PdCl_4$ (aq.) (FIG. 1, part a) and 0.55 mM AA (aq.) (FIG. 1, part b) were recorded. The UV-Vis spectrum of AA showed nearly zero absorbance in the entire tested wave length zone. Compared to AA, $(NH_4)_2PdCl_4$ showed a little higher absorbance, with $\lambda_{max}$ at 403 nm. The UV spectrum of the prepared PdNPs (FIG. 1 part c) showed the typical characteristics of UV-Vis spectrum of reported PdNPs solutions. The UV experiments confirmed the formation of PdNPs upon 15 min of stirring the aqueous mixture solution of AA and $(NH_4)_2PdCl_4$. The prepared PdNPs bulk solution was used for modification of large numbers of GPEs.

Figure 2:
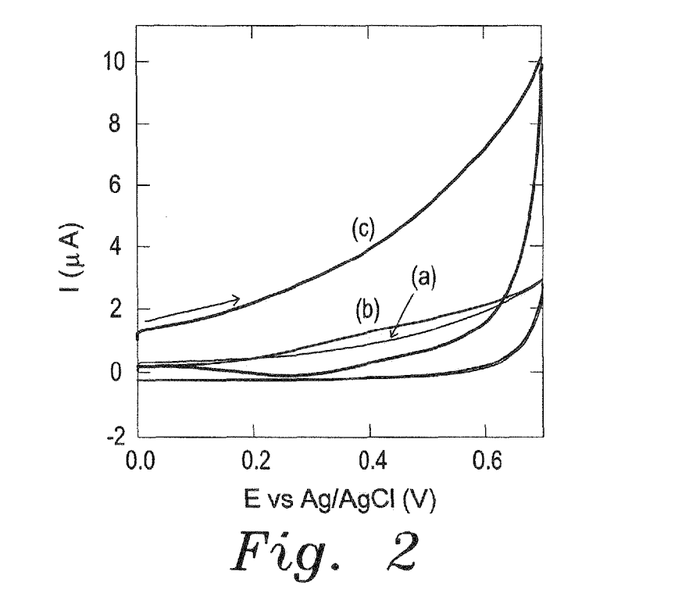
FIG. 2 shows cyclic voltammograms in 0.1 M NaOH aqueous solution of (a) a bare GPE; (b) a PdNP-GPE modified at RT; and (c) a PdNP-GPE modified at 75° C.

Next, a GPE was immersed in the synthesized PdNPs solution and kept for 15 min at RT. After washing and drying, a cyclic voltammogram (CV) of the RT-treated electrode was obtained in 0.1 M NaOH (FIG. 2, part b). The anodic current in the CV (FIG. 2, part b) of the RT-treated GPE is a little higher compared to that obtained for bare GPE (FIG. 2, part a). It is reported that PdNP-modified carbon electrodes show higher anodic current due to formation of hydroxide or oxide on the Pd surface. There are no changes between the cathodic current of the RT-treated GPE and the bare GPE. These results indicate that PdNPs can hardly be attached to the GPE surface from the PdNP solution at RT. For efficient immobilization of PdNPs on GPE surfaces, the temperature is raised from RT to 75° C. by placing the PdNPs solution in which a GPE is immersed into a preheated water bath for 15 min. The CV (FIG. 2, part c) of 75° C.-treated GPE showed the highest anodic current in 0.1 M NaOH. In the cathodic scan of the 75° C.-treated GPE, a hump-type peak at +0.263 V is observed (FIG. 2, part c). These CV experiments suggest that heat treatment plays an important role in immobilizing PdNPs on the GPE.

Figure 3A:
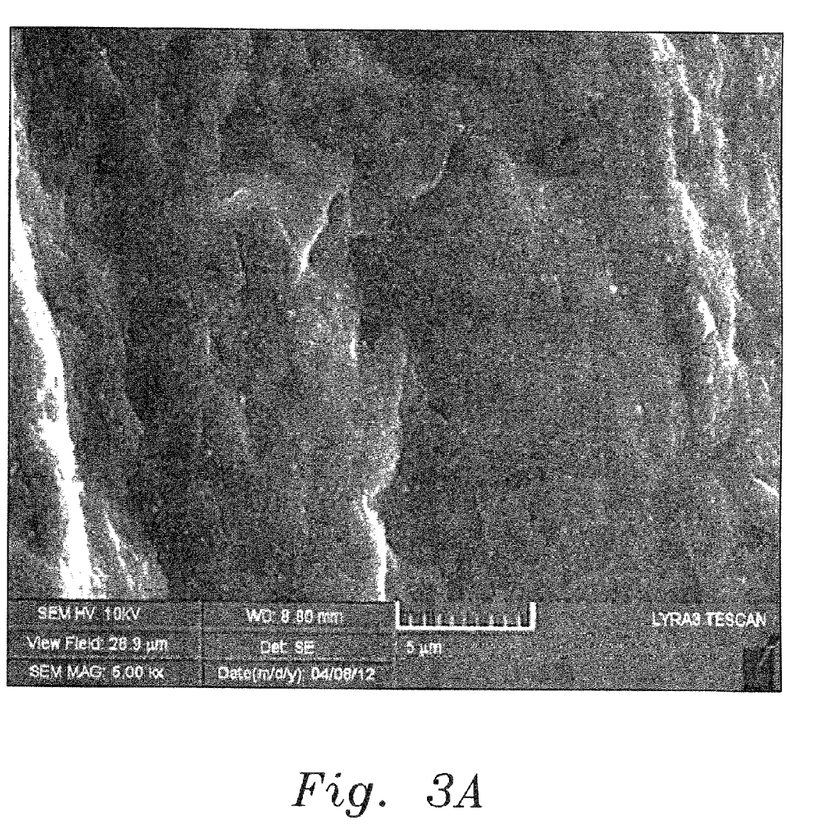
FIG. 3A shows FE-SEM images of a bare GPE at 5 μm magnification.
Figure 3B:
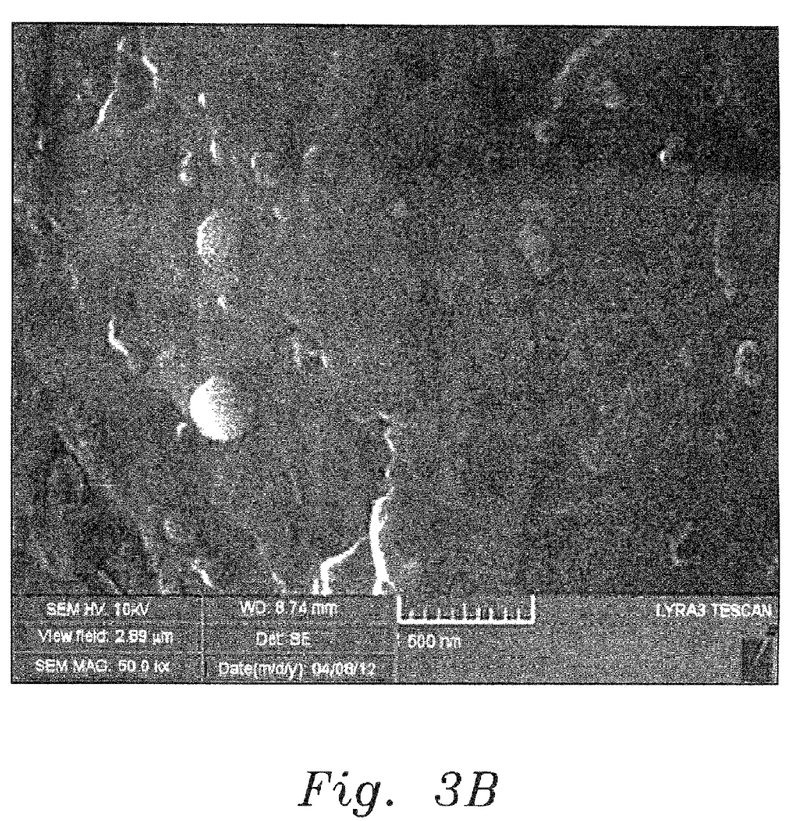
FIG. 3B shows FE-SEM images of a bare GPE at 500 nm magnification.
Figure 3C:
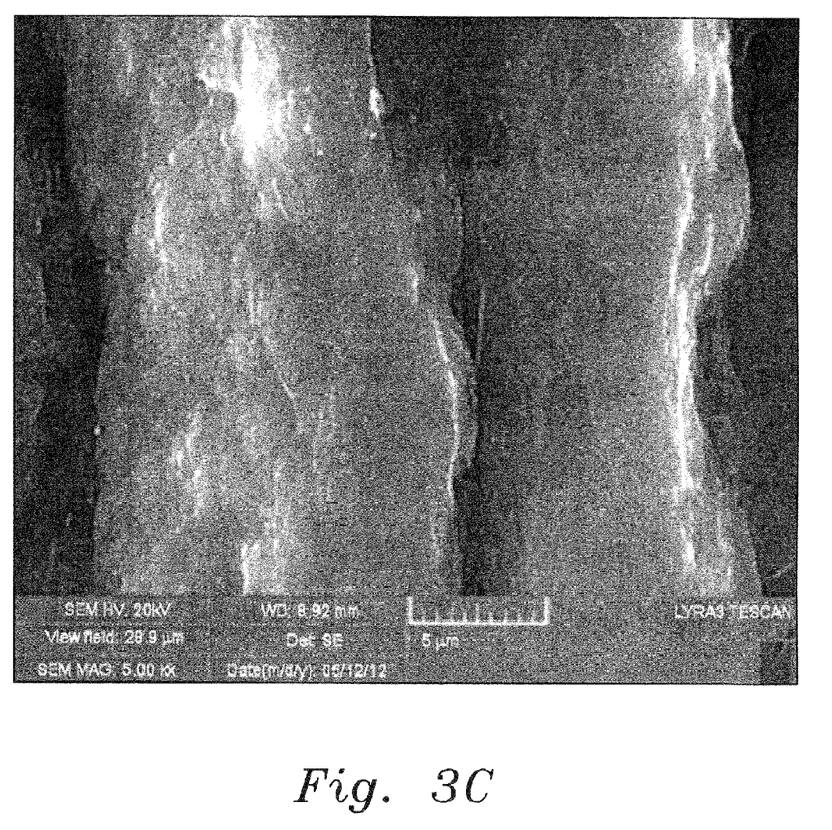
FIG. 3C shows FE-SEM images of a PdNP-GPE modified at RT at 5 μm magnification.
Figure 3D:
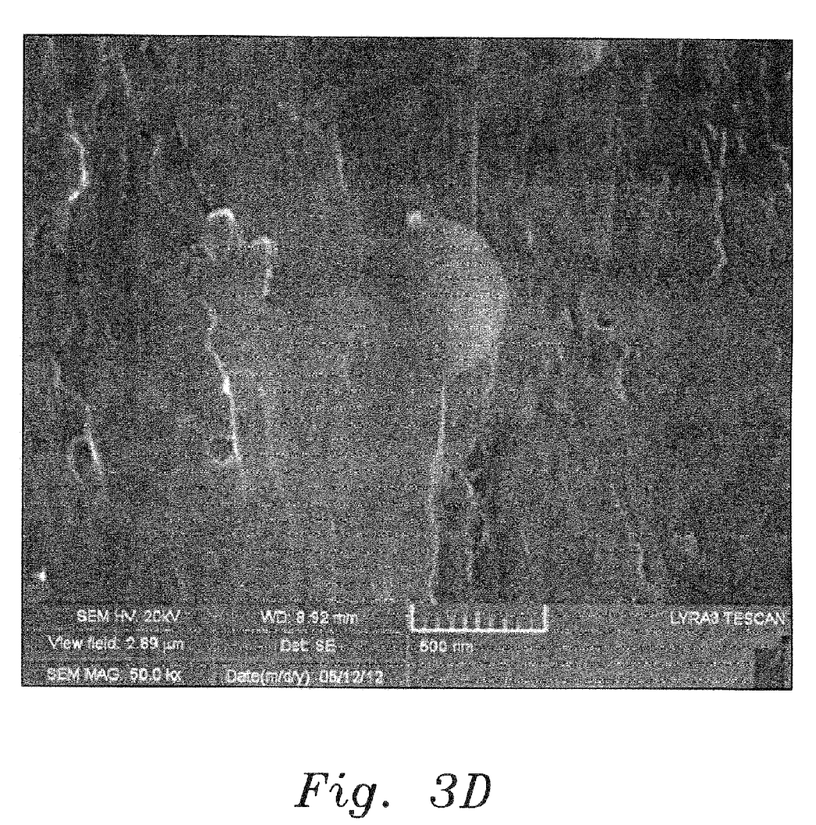
FIG. 3D shows FE-SEM images of a PdNP-GPE modified at RT at 500 nm magnification.
Figure 3E:
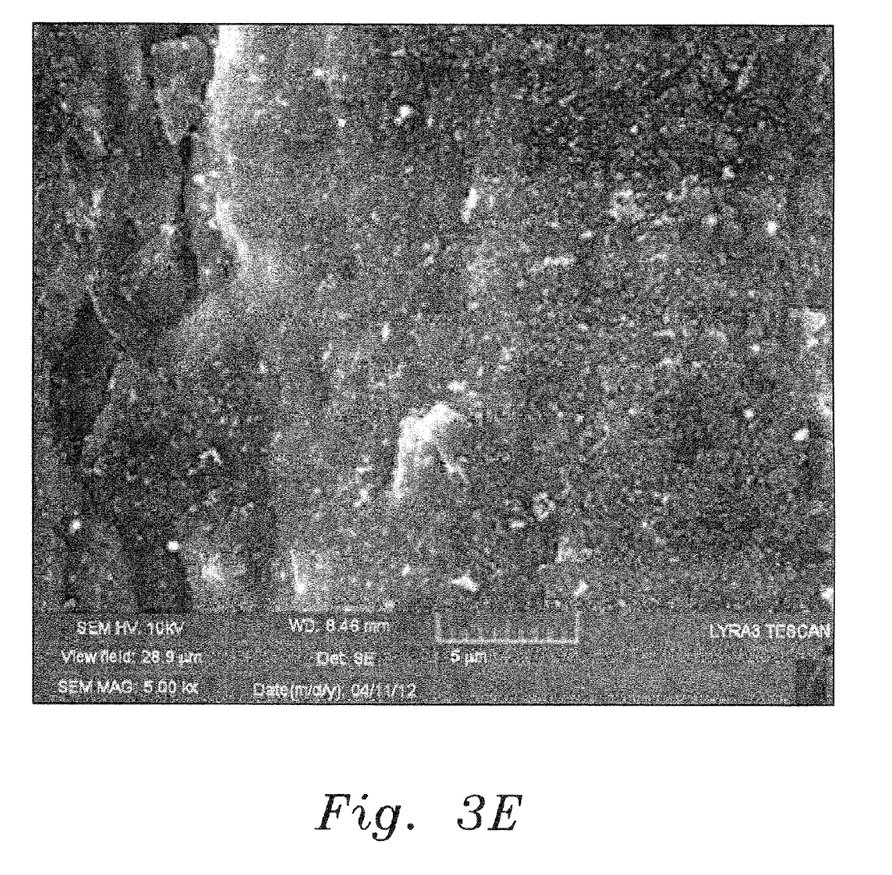
FIG. 3E shows FE-SEM images of a PdNP-GPE modified at 75° C. at 5 μm magnification.
Figure 3F:
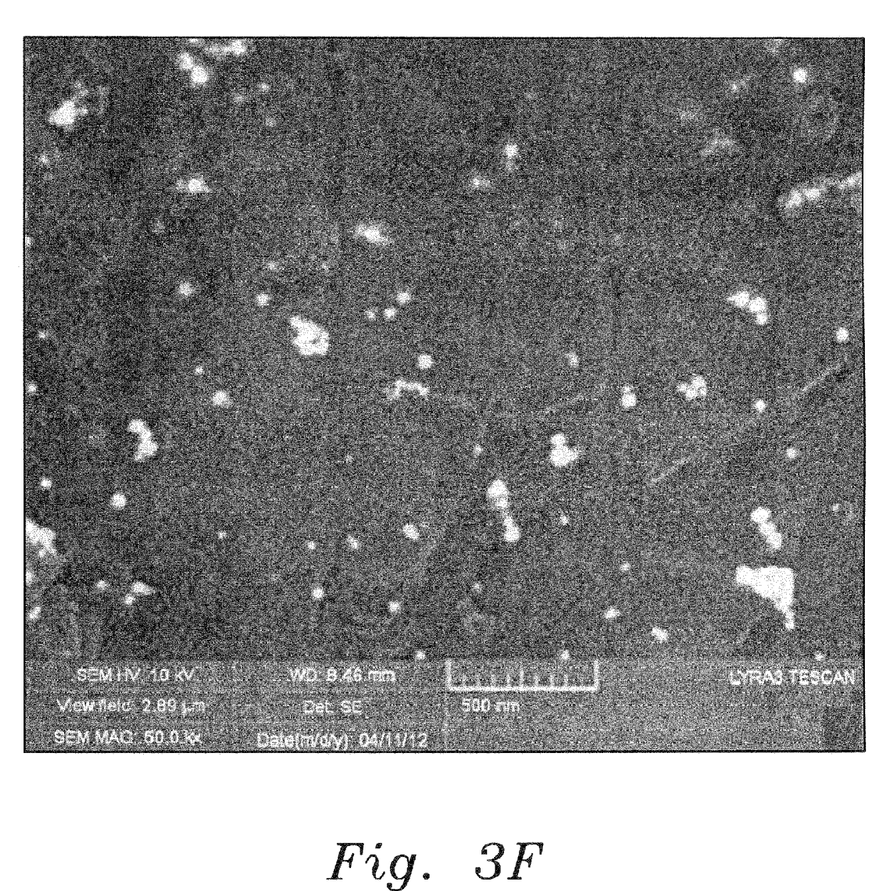
FIG. 3F shows FE-SEM images of a PdNP-GPE modified at 75° C. at 500 nm magnification.

FE-SEM images of a bare GPE, a PdNP-GPE modified at RT, and a PdNP-GPE modified at 75° C. have been recorded at two different magnifications of 5 μm and 500 nm (FIGS. 3A-3F). FIGS. 3A, 3C, and 3E represent the 5 μm magnification FE-SEM images of the bare GPE, the PdNP-GPE modified at RT, and the PdNP-GPE modified at 75° C., respectively. FIGS. 3B, 3D, and 3F represent the 500 nm magnification FE-SEM images of the bare GPE, the PdNP-GPE modified at RT, and the PdNP-GPE modified at 75° C., respectively. FIGS. 3A-3F clearly show that PdNPs are only immobilized on GPE after immersing it in the aqueous solution of PdNPs at 75° C. The low magnified view of the PdNPs-GPE (FIG. 3E) confirms the homogeneous distribution of PdNPs on the surface of PdNP-GPE. The size of the PdNPs on the GPE surface is in the range between 20 to 65 nm (FIG. 3D).

Figure 4:
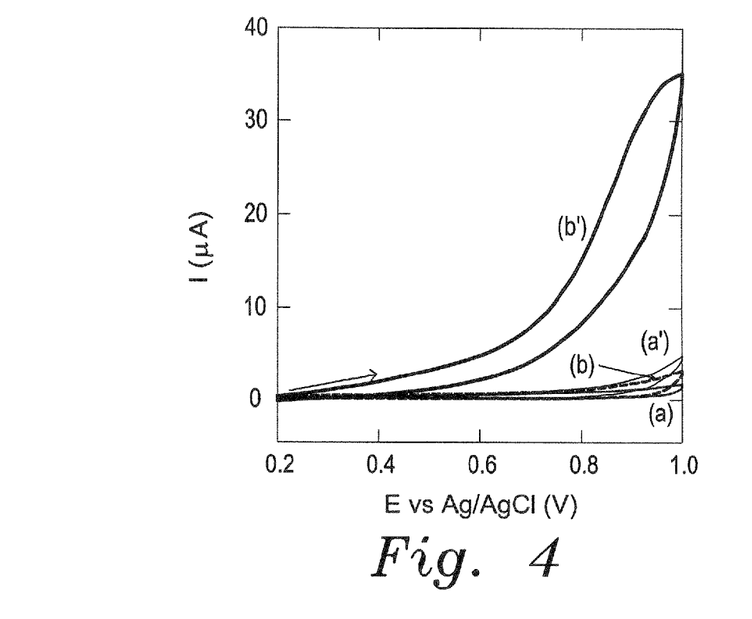
FIG. 4 shows cyclic voltammograms in phosphate buffer solution (0.1 M, pH 7) of (a) a bare GPE in the absence of $H_2O_2$; (b) a Pd-NP-GPE in the absence of $H_2O_2$; (a') a bare GPE in the presence of $H_2O_2$; and (b') a PdNP-GPE in the presence of $H_2O_2$ at a scan rate of 100 mV/s.

To check the effect of the modification of GPE with PdNPs on its electrocatalytic properties, CVs in phosphate buffer (PB) (0.1 M, pH 7) in the absence (FIG. 4, parts a and b) and in the presence of 1.0 mM $H_2O_2$ (FIG. 4, parts a' and b') with bare- (FIG. 4, parts a and a') and PdNP-modified GPEs (FIG. 4, parts b and b') were recorded. From the CV data of FIG. 4, parts a and a', it is confirmed that the bare GPE cannot oxidize $H_2O_2$ at less than +0.5 V and gives poor electrocatalytic properties for electro-oxidation of $H_2O_2$. On the other hand, the background current of PdNP-GPE (FIG. 4, part b) is relatively higher in the anodic scan at around +0.5 V or higher compared to that of bare GPE (FIG. 4, part a). This background increment might be due to hydroxide or oxide formation on the electrode surface. However, the background current of PdNP-GPE is not as high compared to that of bare GPE, whereas the PdNP-GPE (FIG. 4, part b') shows much higher electro-oxidation current of $H_2O_2$ compared to that of bare GPE (FIG. 4, part a'). The oxidation of $H_2O_2$ at the PdNP-GPE has been started from the starting point of the CV which is much lower compared to that of bare GPE, i.e., the PdNP-modified GPE is able to oxidize $H_2O_2$ at lower potentials compared to that of bare GPE. The electro-oxidation of $H_2O_2$ at lower potential on PdNPs-GPE indicates the good electrocatalytic properties of PdNPs. Therefore, PdNPs are suitable as mediators to shuttle electrons between $H_2O_2$ and the GPE, and to facilitate electrochemical generation following electron exchange with hydrogen peroxide.

The reproducibility of the PdNP-modified GPE was tested by recording CVs of seven different modified electrodes in PB containing 1.0 mM $H_2O_2$ (data not shown). The recorded CVs were quite similar, and hence the prepared PdNP-modified GPEs are reproducible and considered a good candidate for electroanalysis of $H_2O_2$.

Figure 5:
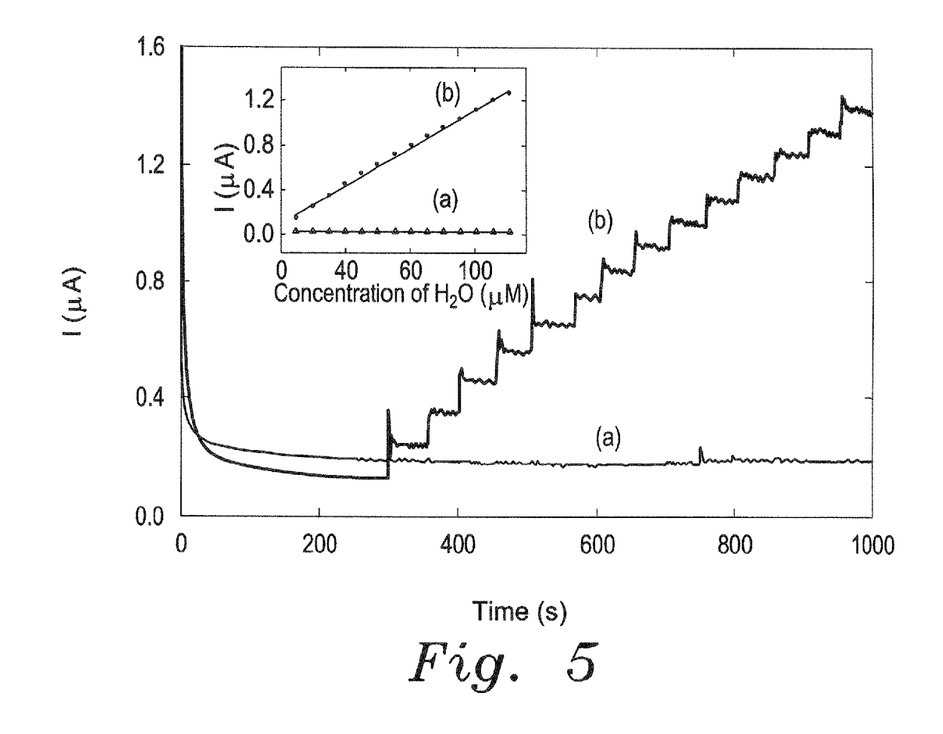
FIG. 5 shows amperometric responses of the (a) bare GPE and (b) PdNP-GPE at +0.8 V upon successive additions of 10 μM $H_2O_2$, the inset showing the corresponding calibration plots.

To obtain $H_2O_2$ concentration dependent signal and detection limit with a bare GPE and a PdNP-modified GPE, an amperometric method has been used. FIG. 5 shows typical amperometric responses of the (part a) bare GPE and (part b) PdNP-modified GPE at +0.8 V upon successive additions of 10 μM $H_2O_2$. The PdNP-modified GPE (FIG. 5, part b) showed well-defined and sensitive signals for each addition of $H_2O_2$, whereas the bare GPE (FIG. 5, part a) gave poor signals. The concentration dependent signal is linear within the entire tested concentration range of $H_2O_2$ for both electrodes (inset of FIG. 5) after subtracting the mean of the corresponding zero hydrogen peroxide response. The PdNP-modified GPE and the bare GPE follow the linear regression equations y=0.077+0.0088x and y=0.0047+0.0000426x, respectively. Here y and x are the amperometric signal and the concentration of $H_2O_2$, respectively. The detection limit of $H_2O_2$ for the PdNP-modified GPE and the bare GPE are 45 nM and 0.58 mM, respectively. The detection limit of hydrogen peroxide determination using the PdNP-modified GPE are comparable, and even better than those obtained using other modified electrodes.

Figure 6:
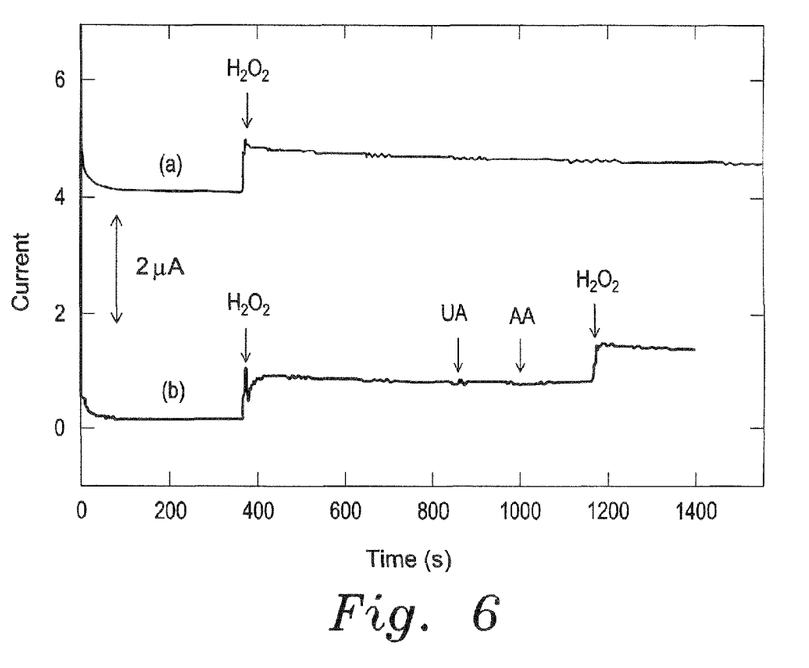
FIG. 6 shows amperometric responses of PdNP-GPE to 100 μM $H_2O_2$ during (a) a prolonged 20 minute experiment, (b) successive additions of hydrogen peroxide ($H_2O_2$), uric acid (UA), and ascorbic acid (AA), and again hydrogen peroxide ($H_2O_2$) at the same PdNP-GPE surface.

The PdNP-modified GPE showed stable and strong catalytic properties that facilitates amperometric measurements of hydrogen peroxide. FIG. 6, part a shows the amperometric response of 100 μM $H_2O_2$ during a prolonged 20.0 minute experiment. The response remains stable throughout the entire experiment, with less than a 10% decrease in the recorded current, indicative of no inhibition effect of $H_2O_2$ and/or its oxidation products at the PdNPs-modified GPE. FIG. 6, part b represents the amperometric response of successive additions of hydrogen peroxide ($H_2O_2$), uric acid (UA) and ascorbic acid (AA), and again $H_2O_2$ at the same PdNP-modified GPE surface. A well-defined $H_2O_2$ response was observed, where subsequent injections of relevant physiological levels (1 μM) of UA and AA did not show any additional signal or even modify the obtained current response. Further spikes of $H_2O_2$ gave a well-defined and reproducible sensor response, reflecting the good selectivity and sensitivity of the fabricated PdNP-modified GPE toward $H_2O_2$ sensing.

The UV experiments were performed using Cintra 303 spectrophotometer (GBC, Sydney, Australia). A Jedo mechanical pencil (Korea) was used as a holder for both bare and PdNP-modified graphite pencil leads. Electrical contact with the lead was achieved by soldering a copper wire to the metallic part that holds the lead in place inside the pencil. The pencil was fixed vertically with 15 mm of the pencil lead extruded outside, and 10 mm of the lead immersed in the solution. Such length corresponds to a geometric electrode area of 15.90 mm$^2$. CHI 660C (CH Instruments Inc. Austin, USA) was used for the entire electrochemical work. The electrochemical cell contained bare- or PdNPs-modified GPE as a working electrode, a Pt wire counter electrode and Ag/AgCl (Sat. KCl) reference electrode. The FE-SEM images were recorded using TESCAN LYRA 3 (Czech Republic).

Ammonium tetrachloropalladate(II), L-ascorbic acid (AA), uric acid (UA) and hydrogen peroxide ($H_2O_2$) were purchased from Sigma-Aldrich (St. Louis, Mo., USA). Disodium hydrogen phosphate and sodium dihydrogen phosphate were supplied by Fisher Scientific Company (USA). Hi-polymer graphite pencil HB black leads were obtained from Pentel Co. LTD. (Japan). All leads had a total length of 60 mm and a diameter of 0.5 mm, and were used as received. All solutions were prepared with deionized water of resistivity of 18.6 MΩcm$^{-1}$, which was obtained directly from PURELAB® Ultra Laboratory Water Purification System (Siemens, Washington, D.C., USA).

EXAMPLE

Equal volumes of 10 ml each aqueous solutions of 1.1 mM ascorbic acid (AA) and 1.0 mM ammonium tetrachloropalladate(II) were mixed with a magnetic stirrer at room temperature (RT) for 15 min to form a palladium nanoparticle solution (PdNPs). A bare GPE was immersed into a 3.0 ml test tube containing the synthesized PdNPs solution. The test tube was placed into a water bath preheated to 75° C. for 15 min. to obtain the PdNPs-modified GPE. The PdNP-GPE was removed and washed by gentle dipping two times in deionized water, then dried at 60° C. for 5 min. prior to use.

The PdNP-GPE exhibits an excellent electrocatalytic activity towards $H_2O_2$ with good reproducibility. With its remarkable electrocatalytic activity, significantly low detection limit, greater analytical selectivity and sensitivity, and response stability, it can be concluded that the quality of the PdNP-modified GPE is excellent and suitable for analytical determination of $H_2O_2$ in various fields.

It is to be understood that the present invention is not limited to the embodiments described above, but encompasses any and all embodiments within the scope of the following claims.

We claim:

1. A method of making a disposable palladium nanoparticle-modified graphite pencil electrode, comprising the steps of:
    mixing an aqueous solution of ascorbic acid with an aqueous solution of ammonium tetrachloropalladate (II) to form a solution containing nanoparticles of palladium;
    immersing a bare graphite pencil lead in the solution containing nanoparticles of palladium; and
    placing a container having the graphite immersed in the solution containing nanoparticles of palladium into a preheated water bath at about 75° C. to form the disposable palladium nanoparticle-modified graphite pencil electrode.

2. The method of making the disposable palladium nanoparticle-modified graphite pencil electrode according to claim 1, further comprising the steps of washing the palladium nanoparticle-modified graphite electrode in deionized water, and then drying the electrode at 60° C.

3. The method of making the disposable palladium nanoparticle-modified graphite pencil electrode according to claim 1, wherein the mixing step is performed at room temperature.

* * * * *